US012586018B2

(12) United States Patent
Whitham et al.

(10) Patent No.: US 12,586,018 B2
(45) Date of Patent: Mar. 24, 2026

(54) SYSTEM AND METHOD FOR CREATING A SERVICE INSTANCE

(71) Applicant: Shopify Inc., Ottawa (CA)

(72) Inventors: Michael Patrick Joseph Whitham, Montreal (CA); Ryan Musgrave, Ottawa (CA)

(73) Assignee: Shopify Inc., Ottawa (CA)

( * ) Notice: Subject to any disclaimer, the term of this patent is extended or adjusted under 35 U.S.C. 154(b) by 299 days.

(21) Appl. No.: 17/155,191

(22) Filed: Jan. 22, 2021

(65) Prior Publication Data

US 2022/0237545 A1 Jul. 28, 2022

(51) Int. Cl.
| | |
|---|---|
| *G16H 50/50* | (2018.01) |
| *G06F 9/38* | (2018.01) |
| *G06Q 10/0631* | (2023.01) |
| *G06Q 30/00* | (2023.01) |
| *G16H 20/40* | (2018.01) |
| *H04L 43/045* | (2022.01) |
| *H04L 12/46* | (2006.01) |

(52) U.S. Cl.
CPC ......... *G06Q 10/06316* (2013.01); *G06F 9/38* (2013.01); *G06F 9/3891* (2013.01); *G06Q 30/00* (2013.01); *G16H 20/40* (2018.01); *G16H 50/50* (2018.01); *H04L 43/045* (2013.01); *H04L 12/46* (2013.01)

(58) Field of Classification Search
CPC .. G06Q 10/06316; G06Q 30/00; G06F 16/95; G06F 8/38; G06F 17/30905; H04L 2463/101

USPC ................................. 705/16, 26, 27.1, 15.51
See application file for complete search history.

(56) References Cited

U.S. PATENT DOCUMENTS

| | | | |
|---|---|---|---|
| 7,330,826 B1* | 2/2008 | Porat .................... | G06Q 50/188 705/37 |
| 8,880,996 B1* | 11/2014 | Deshpande ........ | G06Q 30/0255 715/234 |
| 9,147,004 B2* | 9/2015 | Coursol ............... | G06F 16/958 |
| 10,915,906 B2* | 2/2021 | Keith ................... | G06Q 20/306 |

(Continued)

OTHER PUBLICATIONS

Brian Dougherty, Jules White, Douglas C. Schmidt, Model-driven auto-scaling of green cloud computing infrastructure, Future Generation Computer Systems, vol. 28, Issue 2, 2012, pp. 371-378, (Year: 2012).*

(Continued)

*Primary Examiner* — Patricia H Munson
*Assistant Examiner* — Thea Labogin
(74) *Attorney, Agent, or Firm* — Rowand LLP

(57) ABSTRACT

A computer-implemented method and system for creating a service instance are described. The computer-implemented method may include receiving a request to create a service instance for a service to be executed on a server; determining one or more server operations to complete one or more service configuration tasks in creating the service instance; calculating an estimated time to complete the one or more server operations; determining one or more user configuration tasks to be completed for configuring the service instance based on the estimated time to complete the one or more server operations; and presenting the one or more user configuration tasks to a user for completion while performing the one or more server operations.

21 Claims, 6 Drawing Sheets

(56)  References Cited

U.S. PATENT DOCUMENTS

2018/0240155 A1 *  8/2018  Shaw ................. G06Q 30/0267
2019/0347118 A1 *  11/2019  Mukherjee .......... G06F 9/45512

OTHER PUBLICATIONS

D. Krishnamurthy and J. Rolia. 1998. The internet vs e-commerce
servers: when will server performance matter? In Proceedings of the
1998 conference of the Centre for Advanced Studies on Collabora-
tive research (CASCON '98). IBM Press, 14. (Year: 1998).*
Wang, Xiao Sophia, Arvind Krishnamurthy, and David Wetherall.
"Speeding up web page loads with shandian." 13th {USENIX}
Symposium on Networked Systems Design and Implementation
({NSDI} 16). 2016. (Year: 2016).*
C. Ababei and M. G. Moghaddam, "A Survey of Prediction and
Classification Techniques in Multicore Processor Systems," in IEEE
Transactions on Parallel and Distributed Systems, vol. 30, No. 5, pp.
1184-1200, May 1, 2019, doi: 10.1109/TPDS.2018.2878699. (Year:
2019).*

* cited by examiner

| Server Operation $S_1$ | |
| --- | --- |
| User Configuration Task | Affinity Parameter |
| $t_1$ | 0.8 |
| $t_2$ | 0 |
| $t_3$ | 0.6 |
| . | . |
| . | . |
| . | . |
| $t_n$ | 1 |

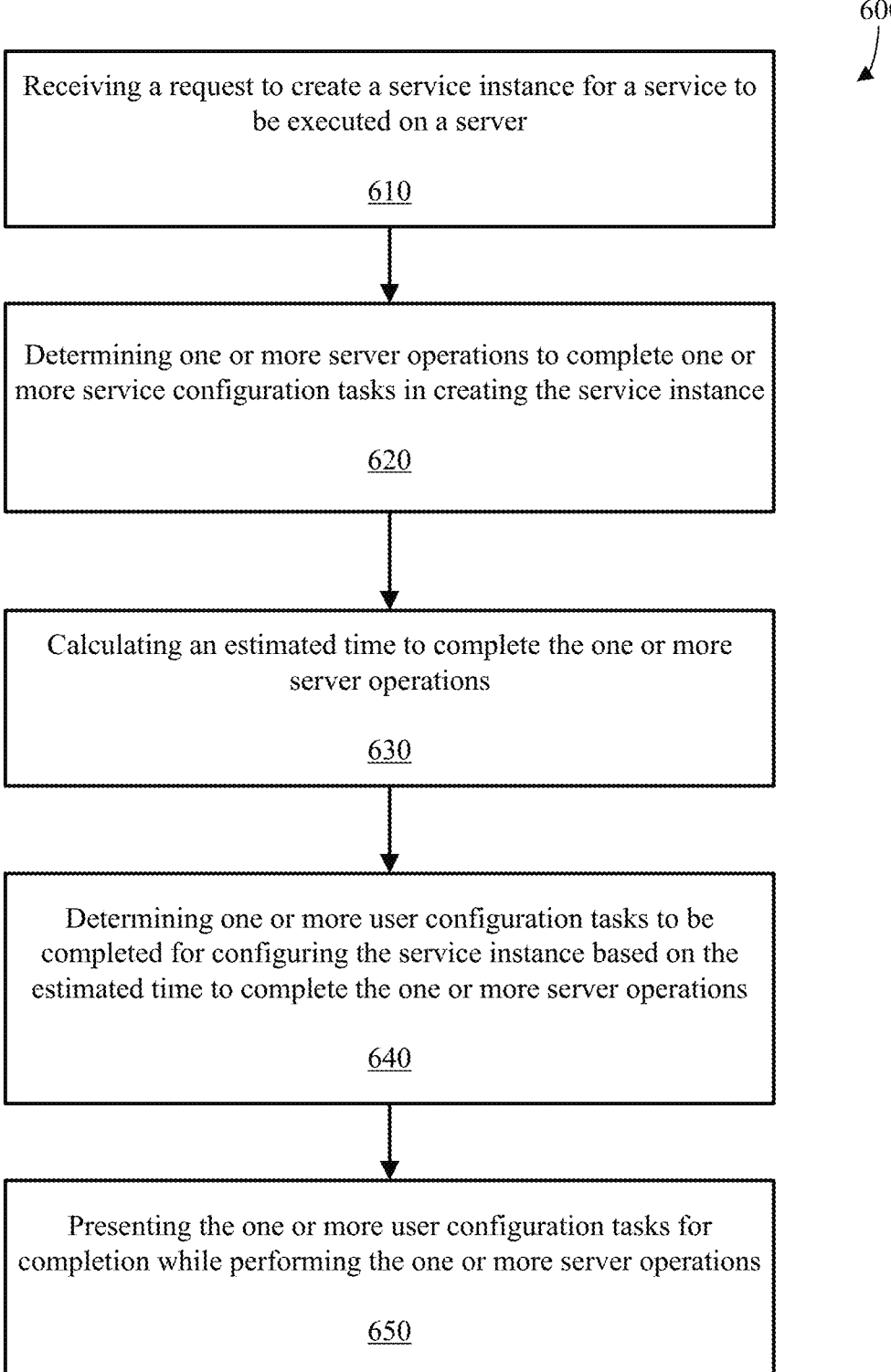

600

Receiving a request to create a service instance for a service to be executed on a server

610

Determining one or more server operations to complete one or more service configuration tasks in creating the service instance

620

Calculating an estimated time to complete the one or more server operations

630

Determining one or more user configuration tasks to be completed for configuring the service instance based on the estimated time to complete the one or more server operations

640

Presenting the one or more user configuration tasks for completion while performing the one or more server operations

SYSTEM AND METHOD FOR CREATING A SERVICE INSTANCE

FIELD

The present disclosure relates to systems and methods for creating a service instance.

BACKGROUND

During creation of a service instance, server operations may be required to complete one or more tasks. Some of these tasks are required to be completed in series.

The time it takes to complete creation of the service instance is only partially based on the time it takes a merchant to complete one or more tasks. The remainder of the time is based on the time it takes to complete one or more server operations.

During longer server processing times, the merchant may be presented with a graphic such as for example a spinner indicating that the system is waiting for one or more servers to complete server operations.

BRIEF DESCRIPTION OF THE DRAWINGS

Embodiments will be described, by way of example only, with reference to the accompanying figures wherein:

FIG. 2 is an example of a home page of an administrator according to an embodiment;

FIG. 6 is a flowchart illustrating an example method for creating a service instance according to an embodiment.

DETAILED DESCRIPTION

Figure 1:
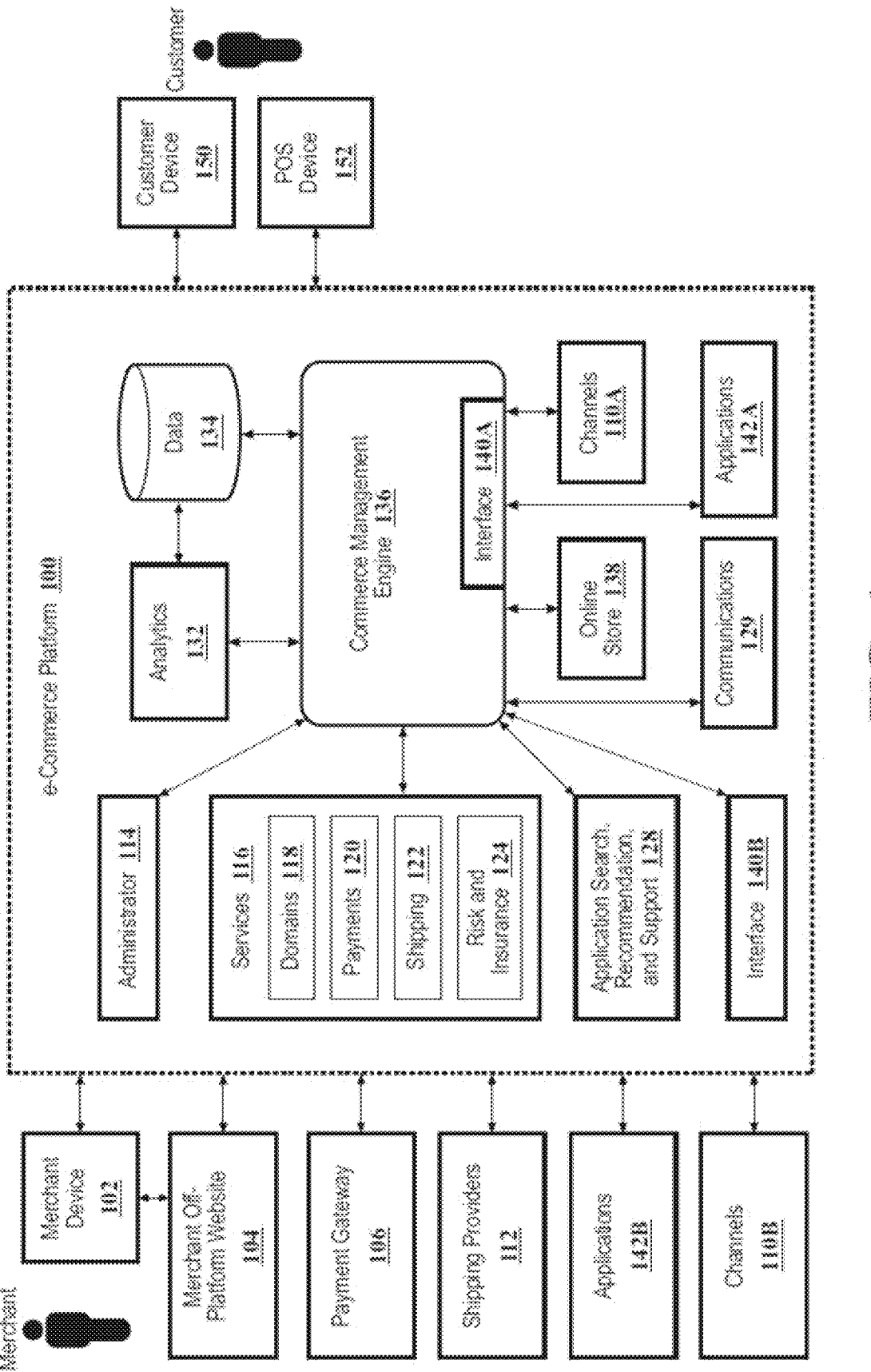
FIG. 1 is a block diagram of an example e-commerce platform according to an embodiment.

In one aspect, the present application describes a computer-implemented method. The method may include receiving a request to create a service instance for a service to be executed on a server; determining one or more server operations to complete one or more service configuration tasks in creating the service instance; calculating an estimated time to complete the one or more server operations; determining one or more user configuration tasks to be completed for configuring the service instance based on the estimated time to complete the one or more server operations; and presenting the one or more user configuration tasks to a user for completion while performing the one or more server operations.

In one or more embodiments, the estimated time to complete the one or more server operations may be based on at least one of network traffic, server load or historical data.

In one or more embodiments, the one or more user configuration tasks may be further determined based on an affinity parameter assigned to the one or more user configuration tasks based on the one or more server operations.

In one or more embodiments, the method may include generating one or more buckets of user configuration tasks for one or more server operations based at least on the affinity parameter.

In one or more embodiments, the user configuration tasks may be included in one or more buckets.

In one or more embodiments, the affinity parameter may be based on a similarity between the one or more user configuration tasks and the one or more server operations.

In one or more embodiments, the one or more user configuration tasks may be further determined based on an estimated time of completion of the one or more user configuration tasks being longer than the estimated time to complete the one or more server operations.

In one or more embodiments, the estimated time of completion of the one or more user configuration tasks may be determined based at least on one or more in-session metrics.

In one or more embodiments, the method may include determining that there are no outstanding user configuration tasks that have an affinity parameter within a threshold; and responsive to determining that there are no outstanding user configuration tasks that have the affinity parameter greater than the threshold, causing a computing device to display a graphic indicating that the system is waiting for the one or more server operations to be completed.

In one or more embodiments, the method may include determining that there are no outstanding user configuration tasks that have an affinity parameter within a threshold; and responsive to determining that there are no outstanding user configuration tasks that have the affinity parameter greater than the threshold, causing a computing device to display an interface including a selectable option to present one or more user configuration tasks to the user for completion while completing the one or more server operations, the one or more user configuration tasks having the affinity parameter outside of the threshold.

In one or more embodiments, the service may include an e-commerce platform and the service instance may include creating a shop on the e-commerce platform.

In another aspect, the present application describes a system. The system may include one or more processors; processor-readable storage medium containing processor-executable instructions that, when executed by the one or more processors, are to cause the one or more processors to receive a request to create a service instance for a service to be executed on a server; determine one or more server operations to complete one or more service configuration tasks in creating the service instance; calculate an estimated time to complete the one or more server operations; determine one or more user configuration tasks to be completed for configuring the service instance based on the estimated time to complete the one or more server operations; and present the one or more user configuration tasks to a user for completion while performing the one or more server operations.

In one or more embodiments, the estimated time to complete the one or more server operations may be based on at least one of network traffic, server load or historical data.

In one or more embodiments, the one or more user configuration tasks may be further determined based on an affinity parameter assigned to the one or more user configuration tasks based on the one or more server operations.

In one or more embodiments, the processor-executable instructions, when executed by the one or more processors, may further cause the one or more processors to generating one or more buckets of user configuration tasks for one or more server operations based at least on the affinity parameter.

In one or more embodiments, the affinity parameter may be based on a similarity between the one or more user configuration tasks and the one or more server operations.

In one or more embodiments, the one or more user configuration tasks may be further determined based on an estimated time of completion of the one or more user configuration tasks being longer than the estimated time to complete the one or more server operations.

In one or more embodiments, the processor-executable instructions, when executed by the one or more processors, may further cause the one or more processors to determine that there are no outstanding user configuration tasks that have an affinity parameter within a threshold; and responsive to determining that there are no outstanding user configuration tasks that have the affinity parameter greater than the threshold, cause a computing device to display a graphic indicating that the system is waiting for the one or more server operations to be completed.

In one or more embodiments, the processor-executable instructions, when executed by the one or more processors, may further cause the one or more processors to determine that there are no outstanding user configuration tasks that have an affinity parameter within a threshold; and responsive to determining that there are no outstanding user configuration tasks that have the affinity parameter greater than the threshold, cause a computing device to display an interface including a selectable option to present one or more user configuration tasks to the user for completion while completing the one or more server operations, the one or more user configuration tasks having the affinity parameter outside of the threshold.

According to another aspect there is provided a non-transitory computer-readable medium storing processor-executable instructions that, when executed by one or more processors, may cause the one or more processors to receive a request to create a service instance for a service to be executed on a server; determine one or more server operations to complete one or more service configuration tasks in creating the service instance; calculate an estimated time to complete the one or more server operations; determine one or more user configuration tasks to be completed for configuring the service instance based on the estimated time to complete the one or more server operations; and present the one or more user configuration tasks to a user for completion while performing the one or more server operations.

For illustrative purposes, specific example embodiments will now be explained in greater detail below in conjunction with the figures.

During creation of a service instance, server operations may be required to complete one or more tasks. Some of these tasks are required to be completed in series which can break up the workflow and lengthen the time it takes to create the service instance.

During longer server processing times, the user may be presented with a graphic such as for example a spinner indicating that the system is waiting for one or more servers to complete server operations. This may create unintended off-ramps for the user as the user may become impatient and cancel the creation of the service instance.

It would be advantageous to reduce the amount of times a graphic such as for example a spinner is presented to the user while still completing server operations.

In accordance with one aspect, the present application provides systems and methods for creating a service instance. The systems and methods may cause a user device to display one or more user configuration tasks for completion while performing the one or more server operations.

The one or more user configuration tasks are displayed in a timely manner and as such the user remains engaged while the one or more server operations are being performed. The one or more user configuration tasks may be selected such that they are related to the one or more server operations being performed. In an example, while a particular server operation is being completed, rather than displaying a graphic indicating to the user that the server is waiting for the particular server operation to be completed, a user configuration task may be presented to the user. In this manner, the service instance (shop creation) is completed in a streamlined manner that reduces the overall time as at least some of the user configuration tasks are completed while server operations are completed in the background.

Example E-Commerce Platform

In the following, a method and system for creating a service instance are described. The service instance may be for a service executed on a server. In some embodiments, the service may include an e-commerce platform and the service instance may be creating a shop or online store on the e-commerce platform. As such, methods disclosed herein may be performed on or in association with an e-commerce platform. An example of an e-commerce platform will be described.

FIG. 1 illustrates an e-commerce platform 100, according to one embodiment. The e-commerce platform 100 may be used to provide merchant products and services to customers. While the disclosure contemplates using the apparatus, system, and process to purchase products and services, for simplicity the description herein will refer to products. All references to products throughout this disclosure should also be understood to be references to products and/or services, including physical products, digital content, tickets, subscriptions, services to be provided, and the like.

While the disclosure throughout contemplates that a 'merchant' and a 'customer' may be more than individuals, for simplicity the description herein may generally refer to merchants and customers (or "purchasers") as such. All references to merchants and customers throughout this disclosure should also be understood to be references to groups of individuals, companies, corporations, computing entities, and the like, and may represent for-profit or not-for-profit exchange of products. Further, while the disclosure throughout refers to 'merchants' and 'customers', and describes their roles as such, the e-commerce platform 100 should be understood to more generally support users in an e-commerce environment, and all references to merchants and customers throughout this disclosure should also be understood to be references to users, such as where a user is a merchant-user (e.g., a seller, retailer, wholesaler, or provider of products), a customer-user (e.g., a buyer, purchase agent, or user of products), a prospective user (e.g., a user browsing and not yet committed to a purchase, a user evaluating the e-commerce platform 100 for potential use in marketing and selling products, and the like), a service provider user (e.g., a shipping provider 112, a financial provider, and the like), a company or corporate user (e.g., a company representative for purchase, sales, or use of products; an enterprise user; a customer relations or customer management agent, and the like), an information technology user, a computing entity user (e.g., a computing bot for purchase, sales, or use of products), and the like.

The e-commerce platform 100 may provide a centralized system for providing merchants with online resources and facilities for managing their business. The facilities described herein may be deployed in part or in whole through a machine that executes computer software, modules, program codes, and/or instructions on one or more processors which may be part of or external to the platform 100. Merchants may utilize the e-commerce platform 100 for managing commerce with customers, such as by implementing an e-commerce experience with customers through an online store 138, through channels 110A-B, through POS devices 152 in physical locations (e.g., a physical storefront or other location such as through a kiosk, terminal, reader, printer, 3D printer, and the like), by managing their business through the e-commerce platform 100, and by interacting with customers through a communications facility 129 of the e-commerce platform 100, or any combination thereof. A merchant may utilize the e-commerce platform 100 as a sole commerce presence with customers, or in conjunction with other merchant commerce facilities, such as through a physical store (e.g., 'brick-and-mortar' retail stores), a merchant off-platform website 104 (e.g., a commerce Internet website or other internet or web property or asset supported by or on behalf of the merchant separately from the e-commerce platform), and the like. However, even these 'other' merchant commerce facilities may be incorporated into the e-commerce platform, such as where POS devices 152 in a physical store of a merchant are linked into the e-commerce platform 100, where a merchant off-platform website 104 is tied into the e-commerce platform 100, such as through 'buy buttons' that link content from the merchant off platform website 104 to the online store 138, and the like.

The online store 138 may represent a multitenant facility comprising a plurality of virtual storefronts. In embodiments, merchants may manage one or more storefronts in the online store 138, such as through a merchant device 102 (e.g., computer, laptop computer, mobile computing device, and the like), and offer products to customers through a number of different channels 110A-B (e.g., an online store 138; a physical storefront through a POS device 152; electronic marketplace, through an electronic buy button integrated into a website or social media channel such as on a social network, social media page, social media messaging system; and the like). A merchant may sell across channels 110A-B and then manage their sales through the e-commerce platform 100, where channels 110A may be provided internal to the e-commerce platform 100 or from outside the e-commerce channel 110B. A merchant may sell in their physical retail store, at pop ups, through wholesale, over the phone, and the like, and then manage their sales through the e-commerce platform 100. A merchant may employ all or any combination of these, such as maintaining a business through a physical storefront utilizing POS devices 152, maintaining a virtual storefront through the online store 138, and utilizing a communication facility 129 to leverage customer interactions and analytics 132 to improve the probability of sales. Throughout this disclosure the terms online store 138 and storefront may be used synonymously to refer to a merchant's online e-commerce offering presence through the e-commerce platform 100, where an online store 138 may refer to the multitenant collection of storefronts supported by the e-commerce platform 100 (e.g., for a plurality of merchants) or to an individual merchant's storefront (e.g., a merchant's online store).

In some embodiments, a customer may interact through a customer device 150 (e.g., computer, laptop computer, mobile computing device, and the like), a POS device 152 (e.g., retail device, a kiosk, an automated checkout system, and the like), or any other commerce interface device known in the art. The e-commerce platform 100 may enable merchants to reach customers through the online store 138, through POS devices 152 in physical locations (e.g., a merchant's storefront or elsewhere), to promote commerce with customers through dialog via electronic communication facility 129, and the like, providing a system for reaching customers and facilitating merchant services for the real or virtual pathways available for reaching and interacting with customers.

In some embodiments, and as described further herein, the e-commerce platform 100 may be implemented through a processing facility including a processor and a memory, the processing facility storing a set of instructions that, when executed, cause the e-commerce platform 100 to perform the e-commerce and support functions as described herein. The processing facility may be part of a server, client, network infrastructure, mobile computing platform, cloud computing platform, stationary computing platform, or other computing platform, and provide electronic connectivity and communications between and amongst the electronic components of the e-commerce platform 100, merchant devices 102, payment gateways 106, application developers, channels 110A-B, shipping providers 112, customer devices 150, point of sale devices 152, and the like. The e-commerce platform 100 may be implemented as a cloud computing service, a software as a service (SaaS), infrastructure as a service (IaaS), platform as a service (PaaS), desktop as a Service (DaaS), managed software as a service (MSaaS), mobile backend as a service (MBaaS), information technology management as a service (ITMaaS), and the like, such as in a software and delivery model in which software is licensed on a subscription basis and centrally hosted (e.g., accessed by users using a client (for example, a thin client) via a web browser or other application, accessed through by POS devices, and the like). In some embodiments, elements of the e-commerce platform 100 may be implemented to operate on various platforms and operating systems, such as iOS, Android, on the web, and the like (e.g., the administrator 114 being implemented in multiple instances for a given online store for iOS, Android, and for the web, each with similar functionality).

In some embodiments, the online store 138 may be served to a customer device 150 through a webpage provided by a server of the e-commerce platform 100. The server may receive a request for the webpage from a browser or other application installed on the customer device 150, where the browser (or other application) connects to the server through an IP Address, the IP address obtained by translating a domain name. In return, the server sends back the requested webpage. Webpages may be written in or include Hypertext Markup Language (HTML), template language, JavaScript, and the like, or any combination thereof. For instance, HTML is a computer language that describes static information for the webpage, such as the layout, format, and content of the webpage. Website designers and developers may use the template language to build webpages that combine static content, which is the same on multiple pages, and dynamic content, which changes from one page to the next. A template language may make it possible to re-use the static elements that define the layout of a webpage, while dynamically populating the page with data from an online store. The static elements may be written in HTML, and the dynamic elements written in the template language. The template language elements in a file may act as placeholders, such that the code in the file is compiled and sent to the customer device 150 and then the template language is replaced by data from the online store 138, such as when a theme is installed. The template and themes may consider tags, objects, and filters. The client device web browser (or other application) then renders the page accordingly.

In some embodiments, online stores 138 may be served by the e-commerce platform 100 to customers, where customers can browse and purchase the various products available (e.g., add them to a cart, purchase immediately through a buy-button, and the like). Online stores 138 may be served to customers in a transparent fashion without customers necessarily being aware that it is being provided through the e-commerce platform 100 (rather than directly from the merchant). Merchants may use a merchant configurable domain name, a customizable HTML theme, and the like, to customize their online store 138. Merchants may customize the look and feel of their website through a theme system, such as where merchants can select and change the look and feel of their online store 138 by changing their theme while having the same underlying product and business data shown within the online store's product hierarchy. Themes may be further customized through a theme editor, a design interface that enables users to customize their website's design with flexibility. Themes may also be customized using theme-specific settings that change aspects, such as specific colors, fonts, and pre-built layout schemes. The online store may implement a content management system for website content. Merchants may author blog posts or static pages and publish them to their online store 138, such as through blogs, articles, and the like, as well as configure navigation menus. Merchants may upload images (e.g., for products), video, content, data, and the like to the e-commerce platform 100, such as for storage by the system (e.g. as data 134). In some embodiments, the e-commerce platform 100 may provide functions for resizing images, associating an image with a product, adding and associating text with an image, adding an image for a new product variant, protecting images, and the like.

As described herein, the e-commerce platform 100 may provide merchants with transactional facilities for products through a number of different channels 110A-B, including the online store 138, over the telephone, as well as through physical POS devices 152 as described herein. The e-commerce platform 100 may include business support services 116, an administrator 114, and the like associated with running an on-line business, such as providing a domain service 118 associated with their online store, payment services 120 for facilitating transactions with a customer, shipping services 122 for providing customer shipping options for purchased products, risk and insurance services 124 associated with product protection and liability, merchant billing, and the like. Services 116 may be provided via the e-commerce platform 100 or in association with external facilities, such as through a payment gateway 106 for payment processing, shipping providers 112 for expediting the shipment of products, and the like.

In some embodiments, the e-commerce platform 100 may provide for integrated shipping services 122 (e.g., through an e-commerce platform shipping facility or through a third-party shipping carrier), such as providing merchants with real-time updates, tracking, automatic rate calculation, bulk order preparation, label printing, and the like.

Figure 2:
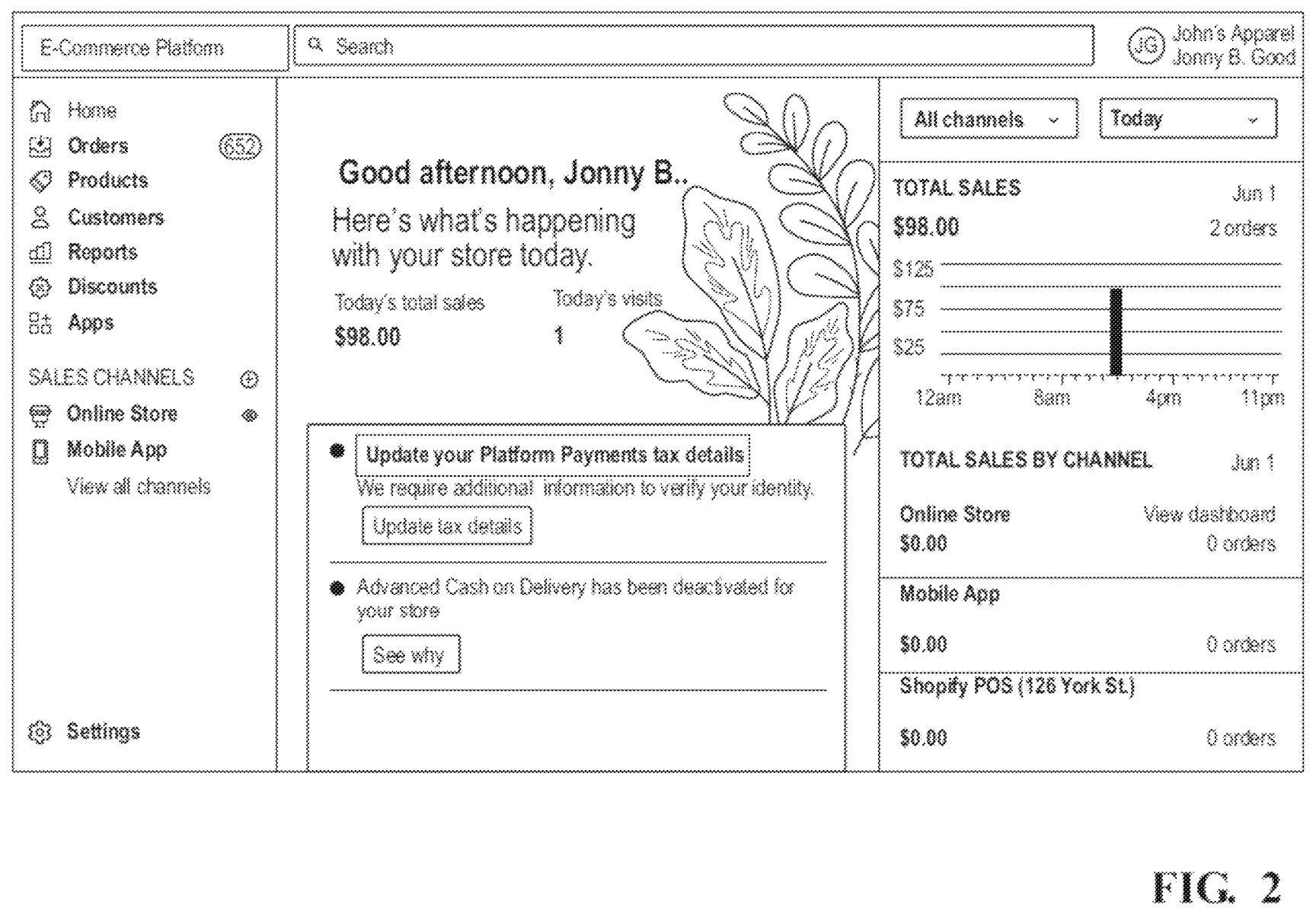

FIG. 2 depicts a non-limiting embodiment for a home page of an administrator 114, which may show information about daily tasks, a store's recent activity, and the next steps a merchant can take to build their business. In some embodiments, a merchant may log in to administrator 114 via a merchant device 102 such as from a desktop computer or mobile device, and manage aspects of their online store 138, such as viewing the online store's 138 recent activity, updating the online store's 138 catalog, managing orders, recent visits activity, total orders activity, and the like. In some embodiments, the merchant may be able to access the different sections of administrator 114 by using the sidebar, such as shown on FIG. 2. Sections of the administrator 114 may include various interfaces for accessing and managing core aspects of a merchant's business, including orders, products, customers, available reports and discounts. The administrator 114 may also include interfaces for managing sales channels for a store including the online store, mobile application(s) made available to customers for accessing the store (Mobile App), POS devices, and/or a buy button. The administrator 114 may also include interfaces for managing applications (Apps) installed on the merchant's account; settings applied to a merchant's online store 138 and account. A merchant may use a search bar to find products, pages, or other information. Depending on the device 102 or software application the merchant is using, they may be enabled for different functionality through the administrator 114. For instance, if a merchant logs in to the administrator 114 from a browser, they may be able to manage all aspects of their online store 138. If the merchant logs in from their mobile device (e.g. via a mobile application), they may be able to view all or a subset of the aspects of their online store 138, such as viewing the online store's 138 recent activity, updating the online store's 138 catalog, managing orders, and the like.

More detailed information about commerce and visitors to a merchant's online store 138 may be viewed through acquisition reports or metrics, such as displaying a sales summary for the merchant's overall business, specific sales and engagement data for active sales channels, and the like. Reports may include, acquisition reports, behavior reports, customer reports, finance reports, marketing reports, sales reports, custom reports, and the like. The merchant may be able to view sales data for different channels 110A-B from different periods of time (e.g., days, weeks, months, and the like), such as by using drop-down menus. An overview dashboard may be provided for a merchant that wants a more detailed view of the store's sales and engagement data. An activity feed in the home metrics section may be provided to illustrate an overview of the activity on the merchant's account. For example, by clicking on a 'view all recent activity' dashboard button, the merchant may be able to see a longer feed of recent activity on their account. A home page may show notifications about the merchant's online store 138, such as based on account status, growth, recent customer activity, and the like. Notifications may be provided to assist a merchant with navigating through a process, such as capturing a payment, marking an order as fulfilled, archiving an order that is complete, and the like.

The e-commerce platform 100 may provide for the communications facility 129 and associated merchant interface for providing electronic communications and marketing, such as utilizing an electronic messaging aggregation facility for collecting and analyzing communication interactions between merchants, customers, merchant devices 102, customer devices 150, POS devices 152, and the like, to aggregate and analyze the communications, such as for increasing the potential for providing a sale of a product, and the like. For instance, a customer may have a question related to a product, which may produce a dialog between the customer and the merchant (or automated processor-based agent representing the merchant), where the communications facility 129 analyzes the interaction and provides analysis to the merchant on how to improve the probability for a sale.

The e-commerce platform 100 may provide a platform payment facility 120 for secure financial transactions with customers, such as through a secure card server environment. The e-commerce platform 100 may store credit card information, such as in payment card industry data (PCI) environments (e.g., a card server), to reconcile financials, bill merchants, perform automated clearing house (ACH) transfers between an e-commerce platform 100 financial institution account and a merchant's bank account (e.g., when using capital), and the like. These systems may have Sarbanes-Oxley Act (SOX) compliance and a high level of diligence required in their development and operation. The platform payment facility 120 may also provide merchants with financial support, such as through the lending of capital (e.g., lending funds, cash advances, and the like) and provision of insurance. In addition, the e-commerce platform 100 may provide for a set of marketing and partner services and control the relationship between the e-commerce platform 100 and partners. They also may connect and onboard new merchants with the e-commerce platform 100. These services may enable merchant growth by making it easier for merchants to work across the e-commerce platform 100. Through these services, merchants may be provided help facilities via the e-commerce platform 100.

In some embodiments, online store 138 may support a great number of independently administered storefronts and process a large volume of transactional data on a daily basis for a variety of products. Transactional data may include customer contact information, billing information, shipping information, information on products purchased, information on services rendered, and any other information associated with business through the e-commerce platform 100. In some embodiments, the e-commerce platform 100 may store this data in a data facility 134. The transactional data may be processed to produce analytics 132, which in turn may be provided to merchants or third-party commerce entities, such as providing consumer trends, marketing and sales insights, recommendations for improving sales, evaluation of customer behaviors, marketing and sales modeling, trends in fraud, and the like, related to online commerce, and provided through dashboard interfaces, through reports, and the like. The e-commerce platform 100 may store information about business and merchant transactions, and the data facility 134 may have many ways of enhancing, contributing, refining, and extracting data, where over time the collected data may enable improvements to aspects of the e-commerce platform 100.

Referring again to FIG. 1, in some embodiments the e-commerce platform 100 may be configured with a commerce management engine 136 for content management, task automation and data management to enable support and services to the plurality of online stores 138 (e.g., related to products, inventory, customers, orders, collaboration, suppliers, reports, financials, risk and fraud, and the like), but be extensible through applications 142A-B that enable greater flexibility and custom processes required for accommodating an ever-growing variety of merchant online stores, POS devices, products, and services, where applications 142A may be provided internal to the e-commerce platform 100 or applications 142B from outside the e-commerce platform 100. In some embodiments, an application 142A may be provided by the same party providing the platform 100 or by a different party. In some embodiments, an application 142B may be provided by the same party providing the platform 100 or by a different party. The commerce management engine 136 may be configured for flexibility and scalability through portioning (e.g., sharing) of functions and data, such as by customer identifier, order identifier, online store identifier, and the like. The commerce management engine 136 may accommodate store-specific business logic and in some embodiments, may incorporate the administrator 114 and/or the online store 138.

The commerce management engine 136 includes base or "core" functions of the e-commerce platform 100, and as such, as described herein, not all functions supporting online stores 138 may be appropriate for inclusion. For instance, functions for inclusion into the commerce management engine 136 may need to exceed a core functionality threshold through which it may be determined that the function is core to a commerce experience (e.g., common to a majority of online store activity, such as across channels, administrator interfaces, merchant locations, industries, product types, and the like), is re-usable across online stores 138 (e.g., functions that can be re-used/modified across core functions), limited to the context of a single online store 138 at a time (e.g., implementing an online store 'isolation principle', where code should not be able to interact with multiple online stores 138 at a time, ensuring that online stores 138 cannot access each other's data), provide a transactional workload, and the like. Maintaining control of what functions are implemented may enable the commerce management engine 136 to remain responsive, as many required features are either served directly by the commerce management engine 136 or enabled through an interface 140A-B, such as by its extension through an application programming interface (API) connection to applications 142A-B and channels 110A-B, where interfaces 140A may be provided to applications 142A and/or channels 110A inside the e-commerce platform 100 or through interfaces 140B provided to applications 142B and/or channels 110B outside the e-commerce platform 100. Generally, the platform 100 may include interfaces 140A-B (which may be extensions, connectors, APIs, and the like) which facilitate connections to and communications with other platforms, systems, software, data sources, code and the like. Such interfaces 140A-B may be an interface 140A of the commerce management engine 136 or an interface 140B of the platform 100 more generally. If care is not given to restricting functionality in the commerce management engine 136, responsiveness could be compromised, such as through infrastructure degradation through slow databases or non-critical backend failures, through catastrophic infrastructure failure such as with a data center going offline, through new code being deployed that takes longer to execute than expected, and the like. To prevent or mitigate these situations, the commerce management engine 136 may be configured to maintain responsiveness, such as through configuration that utilizes timeouts, queues, back-pressure to prevent degradation, and the like.

Although isolating online store data is important to maintaining data privacy between online stores 138 and merchants, there may be reasons for collecting and using cross-store data, such as for example, with an order risk assessment system or a platform payment facility, both of which require information from multiple online stores 138 to perform well. In some embodiments, rather than violating the isolation principle, it may be preferred to move these components out of the commerce management engine 136 and into their own infrastructure within the e-commerce platform 100.

In some embodiments, the e-commerce platform 100 may provide for the platform payment facility 120, which is another example of a component that utilizes data from the commerce management engine 136 but may be located outside so as to not violate the isolation principle. The platform payment facility 120 may allow customers interacting with online stores 138 to have their payment information stored safely by the commerce management engine 136 such that they only have to enter it once. When a customer visits a different online store 138, even if they've never been there before, the platform payment facility 120 may recall their information to enable a more rapid and correct check out. This may provide a cross-platform network effect, where the e-commerce platform 100 becomes more useful to its merchants as more merchants join, such as because there are more customers who checkout more often because of the ease of use with respect to customer purchases. To maximize the effect of this network, payment information for a given customer may be retrievable from an online store's checkout, allowing information to be made available globally across online stores 138. It would be difficult and error prone for each online store 138 to be able to connect to any other online store 138 to retrieve the payment information stored there. As a result, the platform payment facility may be implemented external to the commerce management engine 136.

For those functions that are not included within the commerce management engine 136, applications 142A-B provide a way to add features to the e-commerce platform 100. Applications 142A-B may be able to access and modify data on a merchant's online store 138, perform tasks through the administrator 114, create new flows for a merchant through a user interface (e.g., that is surfaced through extensions/API), and the like. Merchants may be enabled to discover and install applications 142A-B through an application search, recommendations, and support platform 128 or system. In some embodiments, core products, core extension points, applications, and the administrator 114 may be developed to work together. For instance, application extension points may be built inside the administrator 114 so that core features may be extended by way of applications, which may deliver functionality to a merchant through the extension.

In some embodiments, applications 142A-B may deliver functionality to a merchant through the interface 140A-B, such as where an application 142A-B is able to surface transaction data to a merchant (e.g., App: "Engine, surface my app data in mobile and web admin using the embedded app SDK"), and/or where the commerce management engine 136 is able to ask the application to perform work on demand (Engine: "App, give me a local tax calculation for this checkout").

Applications 142A-B may support online stores 138 and channels 110A-B, provide for merchant support, integrate with other services, and the like. Where the commerce management engine 136 may provide the foundation of services to the online store 138, the applications 142A-B may provide a way for merchants to satisfy specific and sometimes unique needs. Different merchants will have different needs, and so may benefit from different applications 142A-B. Applications 142A-B may be better discovered through the e-commerce platform 100 through development of an application taxonomy (categories) that enable applications to be tagged according to a type of function it performs for a merchant; through application data services that support searching, ranking, and recommendation models; through application discovery interfaces such as an application store, home information cards, an application settings page; and the like.

Applications 142A-B may be connected to the commerce management engine 136 through an interface 140A-B, such as utilizing APIs to expose the functionality and data available through and within the commerce management engine 136 to the functionality of applications (e.g., through REST, GraphQL, and the like). For instance, the e-commerce platform 100 may provide API interfaces 140A-B to merchant and partner-facing products and services, such as including application extensions, process flow services, developer-facing resources, and the like. With customers more frequently using mobile devices for shopping, applications 142A-B related to mobile use may benefit from more extensive use of APIs to support the related growing commerce traffic. The flexibility offered through use of applications and APIs (e.g., as offered for application development) enable the e-commerce platform 100 to better accommodate new and unique needs of merchants (and internal developers through internal APIs) without requiring constant change to the commerce management engine 136, thus providing merchants what they need when they need it. For instance, shipping services 122 may be integrated with the commerce management engine 136 through a shipping or carrier service API, thus enabling the e-commerce platform 100 to provide shipping service functionality without directly impacting code running in the commerce management engine 136.

Many merchant problems may be solved by letting partners improve and extend merchant workflows through application development, such as problems associated with back-office operations (merchant-facing applications 142A-B) and in the online store 138 (customer-facing applications 142A-B). As a part of doing business, many merchants will use mobile and web related applications on a daily basis for back-office tasks (e.g., merchandising, inventory, discounts, fulfillment, and the like) and online store tasks (e.g., applications related to their online shop, for flash-sales, new product offerings, and the like), where applications 142A-B, through extension/API 140A-B, help make products easy to view and purchase in a fast growing marketplace. In some embodiments, partners, application developers, internal applications facilities, and the like, may be provided with a software development kit (SDK), such as through creating a frame within the administrator 114 that sandboxes an application interface. In some embodiments, the administrator 114 may not have control over nor be aware of what happens within the frame. The SDK may be used in conjunction with a user interface kit to produce interfaces that mimic the look and feel of the e-commerce platform 100, such as acting as an extension of the commerce management engine 136.

Applications 142A-B that utilize APIs may pull data on demand, but often they also need to have data pushed when updates occur. Update events may be implemented in a subscription model, such as for example, customer creation, product changes, or order cancellation. Update events may provide merchants with needed updates with respect to a changed state of the commerce management engine 136, such as for synchronizing a local database, notifying an external integration partner, and the like. Update events may enable this functionality without having to poll the commerce management engine 136 all the time to check for updates, such as through an update event subscription. In some embodiments, when a change related to an update event subscription occurs, the commerce management engine 136 may post a request, such as to a predefined callback URL. The body of this request may contain a new state of the object and a description of the action or event. Update event subscriptions may be created manually, in the administrator facility 114, or automatically (e.g., via the API 140A-B). In some embodiments, update events may be queued and processed asynchronously from a state change that triggered them, which may produce an update event notification that is not distributed in real-time.

In some embodiments, the e-commerce platform 100 may provide the application search, recommendation and support platform 128. The application search, recommendation and support platform 128 may include developer products and tools to aid in the development of applications, an application dashboard (e.g., to provide developers with a development interface, to administrators for management of applications, to merchants for customization of applications, and the like), facilities for installing and providing permissions with respect to providing access to an application 142A-B (e.g., for public access, such as where criteria must be met before being installed, or for private use by a merchant), application searching to make it easy for a merchant to search for applications 142A-B that satisfy a need for their online store 138, application recommendations to provide merchants with suggestions on how they can improve the user experience through their online store 138, a description of core application capabilities within the commerce management engine 136, and the like. These support facilities may be utilized by application development performed by any entity, including the merchant developing their own application 142A-B, a third-party developer developing an application 142A-B (e.g., contracted by a merchant, developed on their own to offer to the public, contracted for use in association with the e-commerce platform 100, and the like), or an application 142A or 142B being developed by internal personal resources associated with the e-commerce platform 100. In some embodiments, applications 142A-B may be assigned an application identifier (ID), such as for linking to an application (e.g., through an API), searching for an application, making application recommendations, and the like.

The commerce management engine 136 may include base functions of the e-commerce platform 100 and expose these functions through APIs 140A-B to applications 142A-B. The APIs 140A-B may enable different types of applications built through application development. Applications 142A-B may be capable of satisfying a great variety of needs for merchants but may be grouped roughly into three categories: customer-facing applications, merchant-facing applications, integration applications, and the like. Customer-facing applications 142A-B may include online store 138 or channels 110A-B that are places where merchants can list products and have them purchased (e.g., the online store, applications for flash sales (e.g., merchant products or from opportunistic sales opportunities from third-party sources), a mobile store application, a social media channel, an application for providing wholesale purchasing, and the like). Merchant-facing applications 142A-B may include applications that allow the merchant to administer their online store 138 (e.g., through applications related to the web or website or to mobile devices), run their business (e.g., through applications related to POS devices), to grow their business (e.g., through applications related to shipping (e.g., drop shipping), use of automated agents, use of process flow development and improvements), and the like. Integration applications may include applications that provide useful integrations that participate in the running of a business, such as shipping providers 112 and payment gateways.

In some embodiments, an application developer may use an application proxy to fetch data from an outside location and display it on the page of an online store 138. Content on these proxy pages may be dynamic, capable of being updated, and the like. Application proxies may be useful for displaying image galleries, statistics, custom forms, and other kinds of dynamic content. The core-application structure of the e-commerce platform 100 may allow for an increasing number of merchant experiences to be built in applications 142A-B so that the commerce management engine 136 can remain focused on the more commonly utilized business logic of commerce.

The e-commerce platform 100 provides an online shopping experience through a curated system architecture that enables merchants to connect with customers in a flexible and transparent manner. A typical customer experience may be better understood through an embodiment example purchase workflow, where the customer browses the merchant's products on a channel 110A-B, adds what they intend to buy to their cart, proceeds to checkout, and pays for the content of their cart resulting in the creation of an order for the merchant. The merchant may then review and fulfill (or cancel) the order. The product is then delivered to the customer. If the customer is not satisfied, they might return the products to the merchant.

In an example embodiment, a customer may browse a merchant's products on a channel 110A-B. A channel 110A-B is a place where customers can view and buy products. In some embodiments, channels 110A-B may be modeled as applications 142A-B (a possible exception being the online store 138, which is integrated within the commence management engine 136). A merchandising component may allow merchants to describe what they want to sell and where they sell it. The association between a product and a channel may be modeled as a product publication and accessed by channel applications, such as via a product listing API. A product may have many options, like size and color, and many variants that expand the available options into specific combinations of all the options, like the variant that is extra-small and green, or the variant that is size large and blue. Products may have at least one variant (e.g., a "default variant" is created for a product without any options). To facilitate browsing and management, products may be grouped into collections, provided product identifiers (e.g., stock keeping unit (SKU)) and the like. Collections of products may be built by either manually categorizing products into one (e.g., a custom collection), by building rulesets for automatic classification (e.g., a smart collection), and the like. Products may be viewed as 2D images, 3D images, rotating view images, through a virtual or augmented reality interface, and the like.

In some embodiments, the customer may add what they intend to buy to their cart (in an alternate embodiment, a product may be purchased directly, such as through a buy button as described herein). Customers may add product variants to their shopping cart. The shopping cart model may be channel specific. The online store 138 cart may be composed of multiple cart line items, where each cart line item tracks the quantity for a product variant. Merchants may use cart scripts to offer special promotions to customers based on the content of their cart. Since adding a product to a cart does not imply any commitment from the customer or the merchant, and the lifespan of a cart may be in the order of minutes, carts may be persisted to an ephemeral data store in some cases. However, in many implementations, while the customer session may only last minutes, the merchant and/or customer may wish to have the possibility of returning to a cart built in a previous session. Accordingly, the cart, e.g. the shopping cart data structure populated with product item data and a user identifier, may be stored in persistent memory on the platform 100.

In a typical session, a customer proceeds to checkout at some point after adding one or more items to their shopping cart. A checkout component may implement a web checkout as a customer-facing order creation process. A checkout API may be provided as a computer-facing order creation process used by some channel applications to create orders on behalf of customers (e.g., for point of sale). Checkouts may be created from a cart and record a customer's information such as email address, billing, and shipping details. On checkout, the merchant commits to pricing. If the customer does not complete the transaction, the e-commerce platform 100 may retain the shopping cart data structure in memory so that the customer may return to the partially-completed cart in a subsequent session (e.g., in an abandoned cart feature).

Checkouts may calculate taxes and shipping costs based on the customer's shipping address. Checkout may delegate the calculation of taxes to a tax component and the calculation of shipping costs to a delivery component. A pricing component may enable merchants to create discount codes. Discounts may be used by merchants to attract customers and assess the performance of marketing campaigns. Discounts and other custom price systems may be implemented on top of the same platform piece, such as through price rules (e.g., a set of prerequisites that when met imply a set of entitlements). For instance, prerequisites may be items such as "the order subtotal is greater than $100" or "the shipping cost is under $10", and entitlements may be items such as "a 20% discount on the whole order" or "$10 off products X, Y, and Z".

Customers then pay for the content of their cart resulting in the creation of an order for the merchant. Channels 110A-B may use the commerce management engine 136 to move money, currency or a store of value (such as dollars or a cryptocurrency) to and from customers and merchants. Communication with the various payment providers (e.g., online payment systems, mobile payment systems, digital wallet, credit card gateways, and the like) may be implemented within a payment processing component. The actual interactions with the payment gateways 106 may be provided through a card server environment. In some embodiments, the payment gateway 106 may accept international payment, such as integrating with leading international credit card processors. The card server environment may include a card server application, card sink, hosted fields, and the like. This environment may act as the secure gatekeeper of the sensitive credit card information. In some embodiments, most of the process may be orchestrated by a payment processing job. The commerce management engine 136 may support many other payment methods, such as through an offsite payment gateway 106 (e.g., where the customer is redirected to another website), manually (e.g., cash), online payment methods (e.g., online payment systems, mobile payment systems, digital wallet, credit card gateways, and the like), gift cards, and the like. At the end of the checkout process, an order is created. An order is a contract of sale between the merchant and the customer where the merchant agrees to provide the goods and services listed on the orders (e.g., order line items, shipping line items, and the like) and the customer agrees to provide payment (including taxes). This process may be modeled in a sales component. Channels 110A-B that do not rely on commerce management engine 136 checkouts may use an order API to create orders. Once an order is created, an order confirmation notification may be sent to the customer and an order placed notification sent to the merchant via a notification component. Inventory may be reserved when a payment processing job starts to avoid over-selling (e.g., merchants may control this behavior from the inventory policy of each variant). Inventory reservation may have a short time span (minutes) and may need to be very fast and scalable to support flash sales (e.g., a discount or promotion offered for a short time, such as targeting impulse buying). The reservation is released if the payment fails. When the payment succeeds, and an order is created, the reservation is converted into a long-term inventory commitment allocated to a specific location. An inventory component may record where variants are stocked, and tracks quantities for variants that have inventory tracking enabled. It may decouple product variants (a customer facing concept representing the template of a product listing) from inventory items (a merchant facing concept that represents an item whose quantity and location is managed). An inventory level component may keep track of quantities that are available for sale, committed to an order or incoming from an inventory transfer component (e.g., from a vendor).

The merchant may then review and fulfill (or cancel) the order. A review component may implement a business process merchant's use to ensure orders are suitable for fulfillment before actually fulfilling them. Orders may be fraudulent, require verification (e.g., ID checking), have a payment method which requires the merchant to wait to make sure they will receive their funds, and the like. Risks and recommendations may be persisted in an order risk model. Order risks may be generated from a fraud detection tool, submitted by a third-party through an order risk API, and the like. Before proceeding to fulfillment, the merchant may need to capture the payment information (e.g., credit card information) or wait to receive it (e.g., via a bank transfer, check, and the like) and mark the order as paid. The merchant may now prepare the products for delivery. In some embodiments, this business process may be implemented by a fulfillment component. The fulfillment component may group the line items of the order into a logical fulfillment unit of work based on an inventory location and fulfillment service. The merchant may review, adjust the unit of work, and trigger the relevant fulfillment services, such as through a manual fulfillment service (e.g., at merchant managed locations) used when the merchant picks and packs the products in a box, purchase a shipping label and input its tracking number, or just mark the item as fulfilled. A custom fulfillment service may send an email (e.g., a location that doesn't provide an API connection). An API fulfillment service may trigger a third party, where the third-party application creates a fulfillment record. A legacy fulfillment service may trigger a custom API call from the commerce management engine 136 to a third party (e.g., fulfillment by Amazon). A gift card fulfillment service may provision (e.g., generating a number) and activate a gift card. Merchants may use an order printer application to print packing slips. The fulfillment process may be executed when the items are packed in the box and ready for shipping, shipped, tracked, delivered, verified as received by the customer, and the like.

If the customer is not satisfied, they may be able to return the product(s) to the merchant. The business process merchants may go through to "un-sell" an item may be implemented by a return component. Returns may consist of a variety of different actions, such as a restock, where the product that was sold actually comes back into the business and is sellable again; a refund, where the money that was collected from the customer is partially or fully returned; an accounting adjustment noting how much money was refunded (e.g., including if there was any restocking fees, or goods that weren't returned and remain in the customer's hands); and the like. A return may represent a change to the contract of sale (e.g., the order), and where the e-commerce platform 100 may make the merchant aware of compliance issues with respect to legal obligations (e.g., with respect to taxes). In some embodiments, the e-commerce platform 100 may enable merchants to keep track of changes to the contract of sales over time, such as implemented through a sales model component (e.g., an append-only date-based ledger that records sale-related events that happened to an item).

Implementation of Creating a Service Instance Using an E-Commerce Platform

As used herein, the term "shop creation" or "creating a shop" relates to the creation of a shop or online store for an e-commerce platform. In particular embodiments, shop creation may also relate to the modification of a shop or online store on the e-commerce platform.

A user may create a service instance for a service executed on a server. As mentioned, the service may include an e-commerce platform and the service instance may include creating a shop or online store on the e-commerce platform and/or may include a tenant such as for example isolation of data and processing for the user. The server may be a server of the e-commerce system 100.

During shop creation, the e-commerce platform 100 requires the completion of a plurality of tasks. For example, to initiate shop creation, the user may be required to enter an email address, password and a store name. To obtain this information, the e-commerce platform 100 may cause the merchant device 102 to display an interface that includes input fields to be completed by the user. When the user has completed the input fields, the user may select a selectable option to initiate shop creation. In response, the e-commerce platform 100 may initiate shop creation.

The user may then be required to complete a plurality of tasks to get the shop up and running. One or more tasks may be completed through, for example, selecting a settings option within the administrator 114.

A list of tasks required to create the shop may be created. The list may include a preliminary or default list of tasks that must be completed to create the shop. The list may include an ordered sequence of tasks. The list may also include additional tasks that are to be completed based on user selection of shop features to be enabled. The user selection of shop features to be enabled may be updated as shop creation progresses. For example, the user may add or remove shop features as shop creation progresses. As another example, the server may cause the merchant device 102 to display an interface that includes a list of optional tasks. The user may select one or more of the optional tasks as desired.

The tasks may include service configuration tasks and/or user configuration tasks. Service configuration tasks may be dependent on other service configuration tasks. Put another way, some service configuration tasks may have prerequisites and thus must be completed in series. Service configuration tasks may require one or more server operations to be completed. Server operations may include server operations performed by the server of the e-commerce system 100 and/or server operations performed by one or more third party servers. Example service configuration tasks include compliance, financial analysis, business registration number check, tax module configuration, etc. For example, where a service configuration task includes a business registration number check, a business registration number may be entered by the user. Prior to completing one or more other service configuration tasks, the business registration number must be confirmed. As such, a signal may be sent to, for example, to a third party server requesting confirmation of the business registration number. Any service configuration tasks that require a confirmed business registration number cannot be completed until the third party server has confirmed the business registration number.

Figure 3:
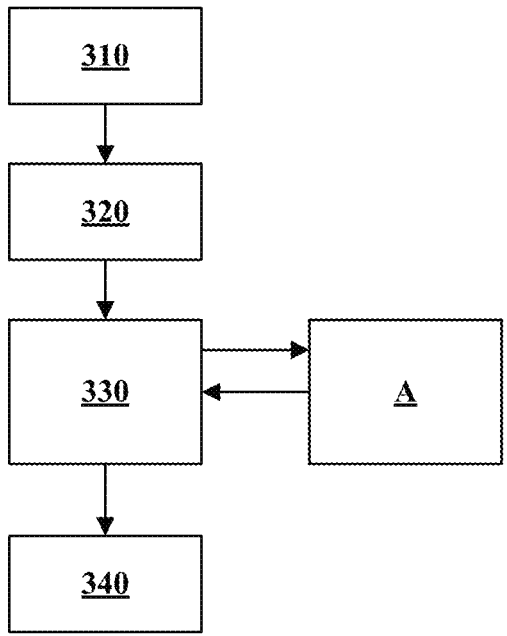
FIG. 3 is a flowchart illustrating example service configuration tasks executed in series according to an embodiment.

Example service configuration tasks are shown in FIG. 3. As can be seen, a first service configuration task 310 is required to be completed before a second service configuration task 320 can be initiated. The second service configuration task 320 is required to be completed before a third service configuration task 330 can be initiated. The third service configuration task 330 requires a server operation to be completed by a server A. When the server A has completed the server operation, the third service configuration task 330 is completed and a fourth service configuration task 340 can be initiated. In this manner, the service configuration tasks 310, 320, 330 and 340 are completed in series.

User configuration tasks may be independent, that is, user configuration tasks may not depend on other user configuration tasks to be completed. Example user configuration tasks may include configuring a "look" of the store by, for example, selecting a template such as a website design template. A website design template may be a predesigned resource that shows structure for the comprehensive layout and display features of the store.

Some of the user configuration tasks may be related to some of the service configuration tasks. Put another way, user configuration tasks may be similar to service configuration tasks in that they may belong to a same category (billing, shipping, etc.). The similarity between user configuration tasks and service configuration tasks may be represented by an affinity parameter.

In this embodiment, the user configuration tasks may be compared to the server operations required to complete the one or more service configuration tasks and an affinity parameter may be assigned accordingly. The affinity parameter may be a number between zero (0) and one (1), where an affinity parameter of zero (0) may indicate that there is no similarity between the server operation and the user configuration task and an affinity parameter of one (1) indicates that there is a strong similarity between the server operation and the user configuration task. The number may be rounded to the nearest tenth, for example.

The similarity between a user configuration task and a server operation may be determined based on a number of factors such as for example a category of the task. For example, a user configuration task and a server operation may both be related to shipping and as such the user configuration task is assigned an affinity parameter of one (1). As another example, a user configuration task may be related to choosing a theme for the appearance of the shop and a server operation may be related to shipping and as such the user configuration task is assigned an affinity parameter of zero (0).

The server may generate a list of all server operations required to complete the service configuration tasks and may similarly generate a list of all user configuration tasks required to create the shop. The user configuration tasks may be compared to the server operations and affinity parameters may be assigned. The results may be stored in look-up tables. Different look-up tables can be used for different server operations. For example, each server operation may have an associated look-up table that may include an affinity parameter for all outstanding user configuration tasks.

Figure 4:
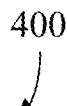
FIG. 4 is a diagram illustrating an example affinity parameter look-up table according to an embodiment.

FIG. 4 is a diagram illustrating an example look-up table 400. The look-up table 400 is specific to a server operation $S_1$. The look-up table 400 defines an affinity parameter for all outstanding user configuration tasks $t_1 \ldots t_n$, the affinity parameter based on a similarity between the server operation $S_1$ and each particular user configuration task $t_1 \ldots t_1$.

In another embodiment, the affinity parameter may be used to generate one or more buckets of user configuration tasks. For example, for a particular server operation, a first bucket may be generated and may include all user configuration tasks that have been assigned an affinity parameter of one (1), a second bucket may be generated and may include all user configuration tasks that have an affinity parameter between 0.5 and 0.9, and a third bucket may be generated and may include all user configuration tasks that have an affinity parameter less than 0.5. In this manner, the first bucket includes all user configuration tasks that are highly similar to the particular server operation, the second bucket includes all user configuration tasks that are somewhat similar to the particular server operation, and the third bucket includes all user configuration tasks that are not similar to the particular server operation.

Figure 5:
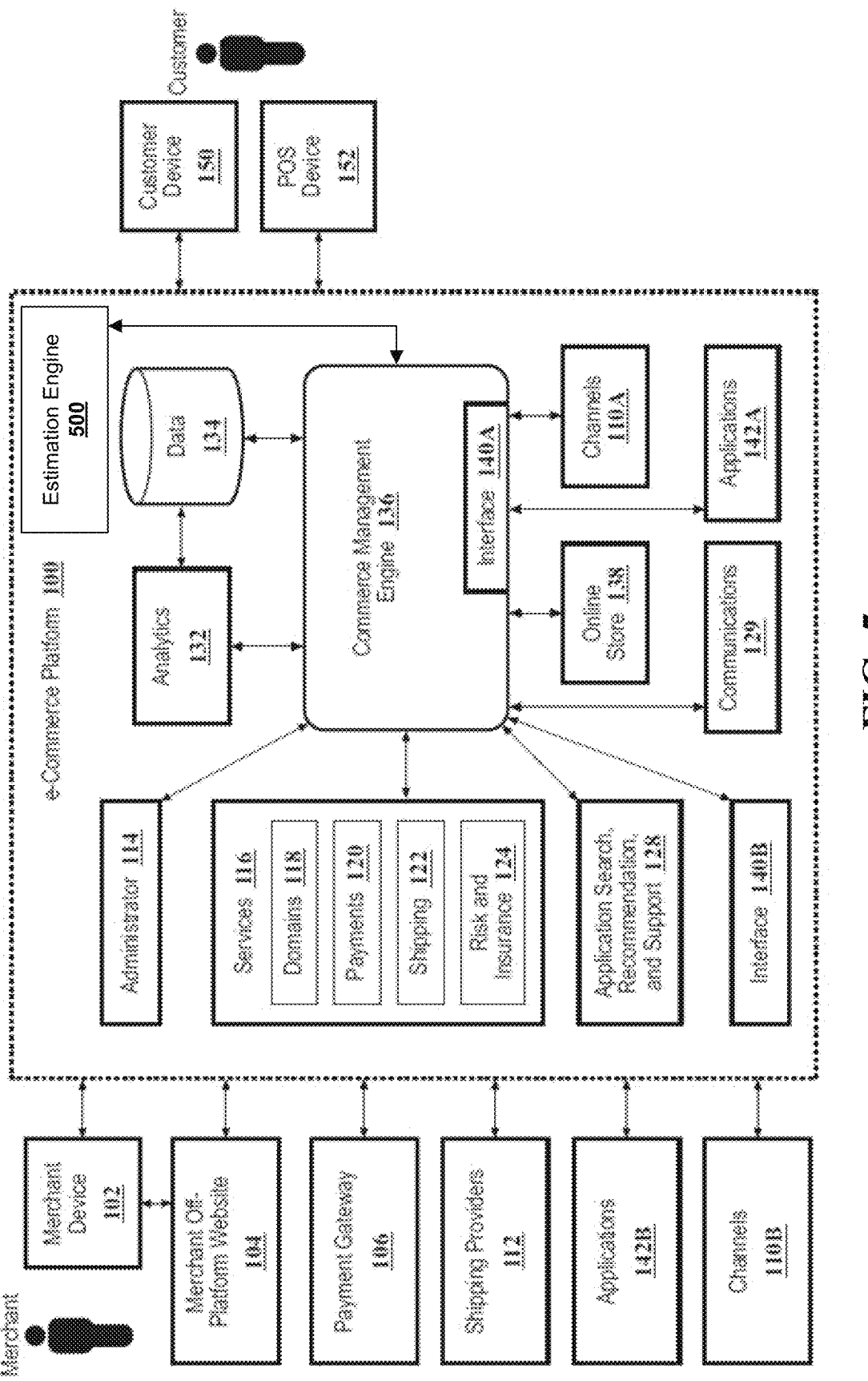
FIG. 5 is a block diagram illustrating an example system for creating a service instance according to an embodiment.

As mentioned, service configuration tasks may require one or more server operations to be completed. The e-commerce platform 100 may calculate an estimated time to complete the one or more server operations. In an embodiment, the estimated time to complete the one or more server operations may be calculated through an estimation engine. FIG. 5 illustrates the e-commerce platform 100 of FIG. 1, but including the estimation engine 500. The estimation engine 500 is an example of a computer-implemented system that estimates time to complete one or more server operations based on one or more factors. The following is a non-limiting list of metrics monitored or determined by the estimation engine 500 to estimate the time to complete one or more server operations:

network traffic;

server load such as third party server load; and historical data such as the average time it took to complete one or more server operations.

Network traffic may include measuring the amount and type of traffic on a particular network and this may be done using one or more known software tools.

Server load may refer to the number of processes or tasks waiting in a queue to access one or more processors of the server. The server load may be calculated over a specific time period and may be expressed as an average. The load average may be expressed as three numbers—representing the server load one minute earlier, five minutes earlier, and fifteen minutes earlier. The server load may be monitored using one or more known software tools.

Historical data may be stored by the estimation engine 500 and may be used to estimate the time to complete one or more server operations. For example, the time it took to complete a particular server operation may be stored as historical data. To calculate an estimated time to complete the particular server operation at a present time, the most recent five (5) recorded times may be averaged and this average may be used to calculate the estimated time. As another example, only the most recent recorded time may be used to calculate the estimated time.

Any one or any combination of these metrics may be used to calculate an estimated time to complete one or more server operations. For example, a lookup table may be used and may include network traffic values and corresponding times it took to complete a particular server operation (based on historical data). As another example, a lookup table may include server load values and corresponding times it took to complete a particular server operation (based on historical data).

The estimation engine 500 may also calculate an estimated time to complete one or more user configuration tasks. For example, the estimation engine 500 may monitor in-session metrics such as for example the average typing speed of the user and this may be used to calculate an estimated time to complete a particular user configuration task. As another example, the time it took the user to complete one or more previous tasks may be used to estimate the time to complete one or more outstanding user configuration tasks. As another example, historical data collected from one or more similar users may be used to estimate the time to complete the one or more user configuration tasks. For example, similar users such as for example users within the same geographic region, users that have a similar shop, etc. may be identified and historical data regarding these similar users may be used to estimate the time to complete the one or more user configuration tasks for the user. It will be appreciated that any one or any combination of these metrics may be used to calculate the estimated time to complete the one or more user configuration tasks.

As mentioned, the server may generate a list of all server operations required to complete the service configuration tasks and may similarly generate a list of all user configuration tasks required to complete shop creation. The estimation engine 500 may analyze the lists and assign estimated times for all server operations and user configuration tasks. As such, all tasks required to create the shop may have an estimated time assigned thereto by the estimation engine 500.

Although the estimations engine is illustrated as a distinct component of the e-commerce platform 100 in FIG. 5, this is only an example. An estimation engine could also or instead be provided by another component of the e-commerce platform 100.

Although the embodiments described below may be implemented in association with the e-commerce platform 100, the embodiments described below are not limited to the specific e-commerce platform 100 of FIGS. 1, 2 and 5. Therefore, the embodiments below will be presented more generally in relation to any e-commerce platform.

As mentioned, a user may create a service instance for a service executed on a server. The service may include an e-commerce platform and the service instance may be creating a shop or online store on the e-commerce platform. An example method 600 for creating a service is described below with reference to FIG. 6. The method 600 may be implemented by a computing device having suitable computer-executable instructions for causing the computing device to carry out the described operations. The instructions may be implemented by way of an application executing on a computing device. The method 600 may be implemented, in whole or in part, by a server that may be part of an e-commerce platform. The server may off-load some operations of the method 600 to a user device such as the merchant device 102 (FIGS. 1 and 5).

The method 600 includes receiving a request to create a service instance for a service to be executed on a server (step 610).

In this embodiment, the request is received from the user device. As mentioned, the service may include an e-commerce platform and the service instance may be creating a shop or online store on the e-commerce platform. The server may be a server associated with the e-commerce platform.

The method 600 includes determining one or more server operations to complete one or more service configuration tasks in creating the service instance (step 620).

The user is required to complete a plurality of tasks to get the shop up and running. The tasks include service configuration tasks and user configuration tasks.

In this embodiment, a list of service configuration tasks required to create the shop is generated by the server. The list includes a preliminary or default list of service configuration tasks that must be completed to create the shop. Put another way, the preliminary or default list of service configuration tasks includes service configuration tasks that must be completed to create a shop.

The list may also include additional service configuration tasks that are to be completed and this may be based on user selection of shop features to be enabled. For example, in response to receiving the request to create the shop, the server may cause the user device to present one or more selectable options to the user, each selectable option being associated with an optional shop feature. The user may select one or more of the optional shop features and the selected shop features may be included in the list of service configuration tasks. The optional shop features may be selected at the beginning of shop creation or may be selected at any time during shop creation.

As mentioned, one or more of the service configuration tasks may be required to be completed in series and as such the list of service tasks may include an ordered sequence of service configuration tasks.

One or more of the service configuration tasks may require one or more server operations to be performed by one or more servers. As such, one or more server operations are determined based on the list of service configuration tasks. The servers required to perform the server operations are thus identified.

The method 600 includes calculating an estimated time to complete the one or more server operations (step 630).

In this embodiment, the estimated time to complete the one or more server operations may be calculated using the estimation engine 500. Specifically, for each server operation determined during step 620, the estimation engine 500 calculates the estimated time to complete the server operation.

As mentioned previously, the estimation engine 500 is a computer-implemented system that estimates time to complete one or more server operations based on one or more factors. The one or more factors include:

network traffic;

server load such as third party server load;

historical data such as the average time it took to complete
        one or more server operations.

As an example, a particular server may be required to complete a server operation. The estimation engine 500 may determine the network traffic and, using this information, may calculate the estimated time to complete the server operation using the particular server. As another example, the estimation engine 500 may determine the server load of the particular server and, using this information, may calculate the estimated time to complete the server operation using the particular server. As another example, the estimation engine 500 may analyze historical data to calculate the estimated time to complete the server operation using the particular server. For example, the estimation engine 500 may determine that the particular server completed a similar operation within the past five (5) minutes and may identify how long it took the particular server to complete the similar operation. The estimated time may then be the time it took the particular server to complete the similar operation. As another example, the most recent five (5) recorded times that the particular server took to complete similar operations may be used by the estimation engine to calculate an average time and this average time may be used as the estimated time.

A combination of network traffic, server load and/or historical data may be used to calculate the estimated time. For example, estimated times may be calculated based on the network traffic, server load and historical data and an average of these three estimated times may calculated.

In this embodiment, the estimated time to complete the one or more server operations are compared to a threshold. The threshold may be, for example, two (2) seconds, five (5) seconds, ten (10) seconds, etc. When the estimated time is greater than the threshold, it is determined that one or more user configuration tasks should be presented to the user while the one or more server operations are being completed. In this manner, rather than presenting the user with a graphic such as a spinner while the server operation is being completed, and thus risk the user exiting out of the shop creation, one or more user configuration tasks may be presented to the user for completion while the one or more server operations are being completed.

The method 600 includes determining one or more user configuration tasks to be completed for configuring the service instance based on the estimated time to complete one or more server operations (step 640).

In this embodiment, a list of user configuration tasks required to create the shop is generated by the server. The list includes a preliminary or default list of user configuration tasks that must be completed to create the shop. Put another way, the preliminary or default list of user configuration tasks includes user configuration tasks that must be completed to create the shop.

The list may also include additional user configuration tasks that are to be completed and this may be based on user selection of shop features to be enabled. For example, in response to receiving the request to create the shop, the server may cause the user device to present one or more selectable options to the user, each selectable option being associated with an optional shop feature. The user may select one or more of the optional shop features and the selected shop features may be included in the list of user configuration tasks.

As mentioned, the estimation engine 500 may calculate an estimated time to complete one or more user configuration tasks. For example, the estimation engine 500 may monitor in-session metrics such as for example the average typing speed of the user and this may be used to calculate an estimated time to complete a particular user configuration task. As another example, the time it took the user to complete one or more previous tasks may be used to estimate the time to complete one or more outstanding user configuration tasks. As another example, historical data collected from one or more similar users may be used to estimate the time to complete the one or more user configuration tasks. For example, similar users such as for example users within the same geographic region, users that have a similar shop, etc. may be identified and historical data regarding these similar users may be used to estimate the time to complete the one or more user configuration tasks for the user. As yet another example, the difference in time between user-generated requests to the server to indicate when a step has been completed in aggregate may be evaluated and this may be used to calculate the estimated time. It will be appreciated that any one or any combination of these metrics may be used to calculate the estimated time to complete the one or more user configuration tasks.

One or more user configuration tasks are determined based on the estimated time to complete the one or more server operations. In this embodiment, the one or more user configuration tasks are determined by comparing the estimated time to complete the one or more user configuration tasks to the estimated time to complete the one or more server operations. A user configuration task having an estimated time of completion greater than the estimated time of completion of the particular server operation may be determined. For example, the estimated time to complete a particular server operation may be fifteen (15) seconds. A user configuration task having an estimated time of completion of greater than fifteen (15) seconds may be determined.

More than one user configuration task may be determined for a particular server operation. For example, the estimated time to complete a particular server operation may be fifteen (15) seconds. A first user configuration task having an estimated time of completion of ten (10) seconds may be determined and a second user configuration task having an estimated time of completion of eight (8) seconds may be determined. As such, the estimated time to complete the first and second user configuration task is eighteen (18) seconds and this is greater than the estimated time to complete the particular server operation (fifteen (15) seconds).

The one or more user configuration tasks may be further determined based on an affinity parameter assigned to the one or more user configuration tasks. For example, as described previously, the user configuration tasks may be compared to the server operations and an affinity parameter may be assigned accordingly. The affinity parameter may indicate a similarity between the one or more user configuration tasks and the one or more server operations. The affinity parameter may be a number between zero (0) and one(1), where an affinity parameter of zero (0) may indicate that there are no similarities between the server operation and the user configuration task and an affinity parameter of one (1) indicates that there is a strong similarity between the server operation and the user configuration task.

The one or more user configuration tasks may be determined when the affinity parameter assigned thereto for a particular server operation is greater than a threshold. For example, only user configuration tasks having an affinity parameter greater than 0.5 may be eligible to be selected for a particular server operation. In this manner, only user configuration tasks that are at least somewhat similar to the server operation being performed may be determined.

The one or more user configuration tasks may be included in one or more buckets. For example, for a particular server operation, a first bucket may be generated and may include all user configuration tasks that have been assigned an affinity parameter of one (1), a second bucket may be generated and may include all user configuration tasks that have an affinity parameter between 0.5 and 0.9, and a third bucket may be generated and may include all user configuration tasks that have an affinity parameter less than 0.5. In this manner, the first bucket includes all user configuration tasks that are highly similar to the particular server operation, the second bucket includes all user configuration tasks that are somewhat similar to the particular server operation, and the third bucket includes all user configuration tasks that are not similar to the particular server operation.

One or more user configuration tasks may be selected from the first bucket as these user configuration tasks have been determined to be highly similar to the particular server operation. When it is determined that the one or more user configuration tasks from the first bucket have been completed, or that no user configuration tasks are in the first bucket, one or more user configuration tasks from the second bucket may be selected as these user configuration tasks have been determined to be at least somewhat similar to the particular server operation. The one or more user configuration tasks may not be selected from the third bucket as these user configuration tasks are not similar to the particular server operation.

It will be appreciated that the user configuration tasks may be included in buckets for more than one particular server operation. When a user configuration task is completed, it may be removed from all buckets.

User configuration tasks may be determined based on the estimated time of completion of the user configuration tasks and based on the affinity parameter assigned to the user configuration tasks for the particular server operation. For example, a user configuration task may be determined by having an estimated time of completion greater than the estimated time of completion for the particular server operation and based on the user configuration task having an affinity parameter greater than 0.5.

The method 600 includes presenting the one or more user configuration tasks for completion while performing the one or more server operations (step 650).

The server may cause the user device to display a user configuration task for completion while performing the one or more server operations. For example, while a particular server operation is being completed, rather than displaying a graphic indicating to the user that the server is waiting for the particular server operation to be completed, a user configuration task may be presented to the user. In this manner, the service instance (shop creation) is completed in a streamlined manner that reduces the overall time as at least some of the user configuration tasks are completed while server operations are completed in the background.

In at least some embodiments, the server may additionally cause the user device to display a graphic such as an indicator, spinner, timer, etc. at the same time as displaying the user configuration task, the graphic indicating that the one or more server operations are being performed. When the graphic is a timer, the timer may be a countdown indicating the estimated time of completion. When the one or more server operations are completed, the graphic may be removed from display and shop creation may return to complete the service configuration tasks when the determined one or more user configuration tasks are completed. In another embodiment, when the one or more server operations are completed, the server may cause the user device to display an indication that includes a selectable option to return to the service configuration tasks and thus stop completion of the presented user configuration task. Progress made on the presented user configuration task may be saved such that the user may return to complete the user configuration task at a later time.

In at least some embodiments, during step 640 of method 600, the affinity parameter or the estimated time of completion of a user configuration task may have higher priority when determining the one or more user configuration tasks. For example, the affinity parameter may have higher priority than the estimated time of completion. In this example, the server may pre-select one or more user configuration tasks based on the affinity parameter and then may select one or more of the pre-selected user configuration tasks based on the estimated time of completion. As another example, only one user configuration task may have an affinity parameter greater than the threshold and thus may be selected. The selected user configuration task may have an estimated time of completion less than the estimated time of completion of the one or more server operations. As such, the server may present the selected user configuration task and, when completed, may cause the user device to display a graphic indicating that the system is waiting for the one or more server operations to be completed.

In at least some embodiments, during step 640 of method 600, the user configuration task having the strongest affinity parameter for a particular server operation may be determined and thus presented to the user for completion.

Although in embodiments, the one or more user configuration tasks are described as being determined when the affinity parameter assigned thereto for a particular server operation is greater than a threshold, in at least some embodiments it may be determined that there are no outstanding user configuration tasks that have an affinity parameter greater than the threshold. When it is determined that there are no outstanding user configuration tasks that have the affinity parameter greater than the threshold, the server may cause the user device to display a graphic indicating that the system is waiting for the one or more server operations to be completed. In this manner, user configuration tasks that are not related to the one or more server operations being completed are not presented to the user and this may help to reduce confusion during shop creation.

In another embodiment, when it is determined that there are no outstanding user configuration tasks that have the affinity parameter greater than the threshold, the server may cause the user device to display an interface including a selectable option to present one or more user configuration tasks to the user for completion while completing the one or more server operations, the one or more user configuration tasks having an affinity parameter less than the threshold. In this manner, user configuration tasks that are not related to the one or more server operations being completed are only presented to the user when the user has indicated that they would like to complete the unrelated user configuration tasks while waiting.

Although in embodiments described above the affinity parameter is described as indicating a similarity between a server operation and a user configuration task, in another embodiment an affinity parameter may indicate a similarity between a service configuration task and a user configuration task.

It will be understood that some of the steps of the example methods described herein may be performed in a different order or simultaneously without materially impacting the operation thereof.

Implementations

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, cloud server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented in different devices which may operate in wired or wireless networks. Examples of wireless networks include 4th Generation (4G) networks (e.g. Long Term Evolution (LTE)) or 5th Generation (5G) networks, as well as non-cellular networks such as Wireless Local Area Networks (WLANs). However, the principles described therein may equally apply to other types of networks.

The operations, methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another, such as from usage data to a normalized usage dataset.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above, and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

What is claimed is:

1. A computer-implemented method performed by one or more processors, the computer-implemented method comprising:

receiving a request to create an online shop on an e-commerce platform executed on a server;

generating a list of one or more service configuration tasks and one or more user configuration tasks required to be completed to create the online shop on the e-commerce platform;

determining one or more server operations to complete the one or more service configuration tasks in creating the online shop on the e-commerce platform;

for each particular server operation:

consulting a look-up table to obtain an affinity parameter assigned to the one or more user configuration tasks, the affinity parameter representing a similarity between the one or more user configuration tasks and the particular server operation;

generating at least one bucket of user configuration tasks based on the affinity parameter assigned to the one or more user configuration tasks;

engaging an estimation engine to determine at least one of a current network traffic or a current server load and to consult a look-up table to calculate an estimated time to complete the particular server operation based on the at least one of the current network traffic or the current server load and historical data; and selecting one or more user configuration tasks from the at least one bucket of user configuration tasks based on the estimated time to complete the particular server operation as calculated by the estimation engine; and creating the online shop on the e-commerce platform by:

performing the one or more server operations; and for each particular server operation, sending, in real-time, the selected one or more user configuration tasks for presentation on a display screen of a user device for completion while the particular server operation is performed in the background.

2. The computer-implemented method of claim 1, wherein the user configuration tasks are included in one or more buckets.

3. The computer-implemented method of claim 1, wherein the one or more user configuration tasks are further determined based on an estimated time of completion of the one or more user configuration tasks being longer than the estimated time to complete the one or more server operations.

4. The computer-implemented method of claim 3, wherein the estimated time of completion of the one or more user configuration tasks is determined based at least on one or more in-session metrics.

5. The computer-implemented method of claim 1, further comprising:

determining that there are no outstanding user configuration tasks that have the affinity parameter within a threshold; and responsive to determining that there are no outstanding user configuration tasks that have the affinity parameter within the threshold, causing the display screen of the user device to display a graphic indicating that the system is waiting for the one or more server operations to be completed.

6. The computer-implemented method of claim 1, further comprising:

determining that there are no outstanding user configuration tasks that have an affinity parameter within a threshold; and responsive to determining that there are no outstanding user configuration tasks that have the affinity parameter within the threshold, causing the display screen of the user device to display an interface including a selectable option to present one or more user configuration tasks to the user for completion while completing the one or more server operations, the one or more user configuration tasks having the affinity parameter outside of the threshold.

7. The computer-implemented method of claim 1, wherein the at least one bucket of user configuration tasks includes a first bucket for user configuration tasks that are highly similar to the particular server operation, a second bucket for user configuration tasks that are somewhat similar to the particular server operation, and a third bucket for user configuration tasks that are not similar to the particular server operation.

8. The computer-implemented method of claim 7, wherein the user configuration tasks of the second bucket are only selected when it is determined that all user configuration tasks of the first bucket have been completed.

9. The computer-implemented method of claim 1, wherein historical data includes at least one time it took to complete the particular server operation at a particular amount of network traffic or server load.

10. The computer-implemented method of claim 1, wherein the historical data includes an average time it took to complete the particular server operation at a particular amount of network traffic or server load.

11. The computer-implemented method of claim 1, wherein at least some of the service configuration tasks are required to be completed in series.

12. A system comprising:
one or more processors;
processor-readable storage medium containing processor-executable instructions that, when executed by the one or more processors, are to cause the one or more processors to:
    receive a request to create an online shop on an e-commerce platform executed on a server;
    generate a list of one or more service configuration tasks and one or more user configuration tasks required to be completed to create the online shop on the e-commerce platform;
    determine one or more server operations to complete the one or more service configuration tasks in creating the online shop on the e-commerce platform;
    for each particular server operation:
        consult a look-up table to obtain an affinity parameter assigned to one or more user configuration tasks, the affinity parameter representing a similarity between the one or more user configuration tasks and the particular server operation;
        generate at least one bucket of user configuration tasks based on the affinity parameter assigned to the one or more user configuration tasks;
        engage an estimation engine to determine at least one of a current network traffic or a current server load and to consult a look-up table to calculate an estimated time to complete the particular server operation based on the at least one of the current network traffic or the current server load and historical data; and
        select one or more user configuration tasks from the at least one bucket of user configuration tasks based on the estimated time to complete the particular server operation as calculated by the estimation engine; and
    create the online shop on the e-commerce platform by:
        performing the one or more server operations; and
        for each particular server operation, sending, in real-time, the selected one or more user configuration tasks for presentation on a display screen of a user device for completion while the particular server operation is performed in the background.

13. The system of claim 12, wherein the one or more user configuration tasks are further determined based on an estimated time of completion of the one or more user configuration tasks being longer than the estimated time to complete the one or more server operations.

14. The system of claim 12, wherein the processor-executable instructions, when executed by the one or more processors, are to further cause the one or more processors to:
    determine that there are no outstanding user configuration tasks that have the affinity parameter within a threshold; and
    responsive to determining that there are no outstanding user configuration tasks that have the affinity parameter within the threshold, cause the display screen of the user device to display a graphic indicating that the system is waiting for the one or more server operations to be completed.

15. The system of claim 12, wherein the processor-executable instructions, when executed by the one or more processors, are to further cause the one or more processors to:
    determine that there are no outstanding user configuration tasks that have an affinity parameter within a threshold; and
    responsive to determining that there are no outstanding user configuration tasks that have the affinity parameter within the threshold, cause the display screen of the user device to display an interface including a selectable option to present one or more user configuration tasks to the user for completion while completing the one or more server operations, the one or more user configuration tasks having the affinity parameter outside of the threshold.

16. The system of claim 12, wherein the at least one bucket of user configuration tasks includes a first bucket for user configuration tasks that are highly similar to the particular server operation, a second bucket for user configuration tasks that are somewhat similar to the particular server operation, and a third bucket for user configuration tasks that are not similar to the particular server operation.

17. The system of claim 16, wherein the user configuration tasks of the second bucket are only selected when it is determined that all user configuration tasks of the first bucket have been completed.

18. The system of claim 12, wherein historical data includes at least one time it took to complete the particular server operation at a particular amount of network traffic or server load.

19. The system of claim 12, wherein the historical data includes an average time it took to complete the particular server operation at a particular amount of network traffic or server load.

20. The system of claim 12, wherein at least some of the service configuration tasks are required to be completed in series.

21. A non-transitory computer-readable medium storing processor-executable instructions that, when executed by one or more processors, are to cause the one or more processors to:
    receive a request to create an online shop on an e-commerce platform executed on a server;
    generate a list of one or more service configuration tasks and one or more user configuration tasks required to be completed to create the online shop on the e-commerce platform;
    determine one or more server operations to complete the one or more service configuration tasks in creating the online shop on the e-commerce platform;
    for each particular server operation:
        consult a look-up table to obtain an affinity parameter assigned to the one or more user configuration tasks, the affinity parameter representing a similarity between the one or more user configuration tasks and the particular server operation;
        generate at least one bucket of user configuration tasks based on the affinity parameter assigned to the one or more user configuration tasks;
        engage an estimation engine to determine at least one of a current network traffic or a current server load and to consult a look-up table to calculate an estimated time to complete the particular server operation based on the at least one of the current network traffic or the current server load and historical data; and select one or more user configuration tasks from the at least one bucket of user configuration tasks based on the estimated time to complete the particular server operation as calculated by the estimation engine; and create the online shop on the e-commerce platform by:

performing the one or more server operations; and for each particular server operation, sending, in real-time, the selected one or more user configuration tasks for presentation on a display screen of a user device for completion while the particular server operation is performed in the background.

*    *    *    *    *